United States Patent
Lewis et al.

(10) Patent No.: US 11,170,668 B2
(45) Date of Patent: Nov. 9, 2021

(54) TAMPER-EVIDENT INDICATOR WRAPS

(71) Applicant: Precision Dynamics Corporation, Valencia, CA (US)

(72) Inventors: Jonathan Lewis, Valencia, CA (US); Ronald G. Ennis, Los Angeles, CA (US)

(73) Assignee: Precision Dynamics Corporation, Valencia, CA (US)

( * ) Notice: Subject to any disclaimer, the term of this patent is extended or adjusted under 35 U.S.C. 154(b) by 0 days.

(21) Appl. No.: 16/882,125

(22) Filed: May 22, 2020

(65) Prior Publication Data

US 2020/0388196 A1  Dec. 10, 2020

Related U.S. Application Data

(60) Provisional application No. 62/859,480, filed on Jun. 10, 2019.

(51) Int. Cl.
*G09F 3/14* (2006.01)
*G09F 3/00* (2006.01)
*A61B 90/92* (2016.01)
*G09F 3/02* (2006.01)

(52) U.S. Cl.
CPC ............. *G09F 3/005* (2013.01); *A61B 90/92* (2016.02); *G09F 3/0292* (2013.01); *G09F 2003/0222* (2013.01); *G09F 2003/0245* (2013.01)

(58) Field of Classification Search
CPC .................. G09F 3/005; G09F 3/0292; G09F 2003/0222; G09F 2003/0245; A61B 90/90

USPC ........................... 40/640, 630, 638, 666, 665
See application file for complete search history.

(56) References Cited

U.S. PATENT DOCUMENTS

| | | | | |
|---|---|---|---|---|
| 3,153,869 A | * | 10/1964 | Twentier | G09F 3/005 40/633 |
| 3,631,617 A | * | 1/1972 | Pekko | B32B 27/08 283/101 |
| 4,246,307 A | * | 1/1981 | Trautwein | B32B 7/14 428/43 |
| 5,013,088 A | * | 5/1991 | Marin | G09F 3/0292 283/101 |
| 5,165,725 A | * | 11/1992 | Gollon | G09F 3/0292 283/108 |
| D598,319 S | | 8/2009 | Joseph | |
| 7,765,728 B1 | * | 8/2010 | Waggoner | G09F 3/005 40/633 |
| D656,431 S | | 3/2012 | Bekker | |
| 2010/0327002 A1 | * | 12/2010 | Hegan | G09F 3/005 221/30 |

* cited by examiner

*Primary Examiner* — Cassandra Davis
(74) *Attorney, Agent, or Firm* — Quarles & Brady LLP

(57) ABSTRACT

Systems and methods include tamper-evident indicators applied to a band comprising a strap that forms a closed loop. Tamper-evident sections of the indicators provide increased security against accidental and intentional removal of the indicators. Indicators are provided with adhesives and bare areas devoid of adhesive allowing easy and secure application of indicators to bands while they are being worn and with greater ease. Indicators can be further provided with liners protecting the adhesives allowing the indicators to be easily applied by gloved hands, reducing contamination risks. Contamination and wear risks can be further reduced by supplying indicators with antimicrobial surfaces and overprint varnishing.

16 Claims, 2 Drawing Sheets

TAMPER-EVIDENT INDICATOR WRAPS

CROSS-REFERENCE TO RELATED APPLICATION

This application claims the benefit of U.S. Provisional Patent Application No. 62/859,480 entitled "Tamper-Evident Indicator Wraps" filed on Jun. 10, 2019, the entire contents of which are incorporated herein by reference.

FIELD OF INVENTION

This disclosure relates to attaching visible indicators to bands such as, for example, wristbands that can be attached to objects or worn around limbs of people or animals.

BACKGROUND

Wrist and ankle bands are commonly worn by people or animals for identification and other purposes. One common application of such bands is as patient identification bands worn by patients in hospital and other medical settings. In such settings, patient identification bands are frequently augmented with indicators to alert medical personnel to patient conditions such as medication allergies, bleeding disorders, fall risks, and so forth.

Conventional approaches to augmenting bands such as those worn as patient identification bands include using supplemental bands fastened around a patient's wrist or ankle. These supplemental bands are used as indicators that may be labeled or colored to identify the indication they are meant to communicate. Other conventional approaches include attaching indicator stickers to an identification band or attaching specialized indicator devices (such as plastic indicators which snap closed or snap onto raised nubs using friction fittings) to an identification band.

SUMMARY

Conventional approaches such as those described above have disadvantages, particularly in the medical field. The use of one or more supplemental indicator bands in addition to an identification band can be uncomfortable for patients and may result in the patient intentionally or unintentionally removing an important indicator whose removal cannot be readily detected. Moreover, conventional stickers and supplementary bands may also fall off due to repeated rubbing against or snagging on other objects and require replacement. Furthermore, stickers may be difficult to apply be medical personnel wearing surgical gloves. In addition, the adhesive backings of stickers may accidentally contact the patient's skin or hair on the skin, causing discomfort and increasing the likelihood that the sticker will separate from the identification band.

Provided herein is a novel structure for supplemental identification on bands that addresses many of aforementioned issues and provides an improved mode of attachment.

According to one aspect, an assembly is provided having a band including a strap that forms a closed loop and a set of one or more flexible tamper-evident indicators. The indicators are formed from respective lengths of flexible indicator material. Each indicator has first and second ends and is adhesively fastened by adhesives disposed at these first and second ends to the band at a respective location on the strap. The respective location on the strap has a width smaller than each of the respective lengths of flexible indicator material.

In some forms, the adhesives may be disposed on an underside of each indicator and each indicator may be configured such that a partial top surface of that indicator overlays an outwardly-facing surface of the strap at the first and second ends of that indicator. The partial top surface may bear an indicium (such as text or images, for example, and may be associated with the condition of the wearer so as to indicate, for example, a fall risk, an allergy, and so on). The outwardly-facing surface of the strap and the partial top surface of each indicator may face away from a center of the closed loop. Put differently, the ends may be adhesively secured to the band on an outer surface of the band so the terminal ends are visible when the band is worn.

In some forms, the set of one or more flexible tamper-evident indicators may include a first and second indicator. The first indicator may have a first color and bear a first indicium on its partial top surface while the second indicator may have a second color and bear a second indicium on its partial top surface.

In some forms, the indicators and the adhesives may be jointly configured and dimensioned such that removal of any indicator causes at least a portion of the partial top surface of that indicator having a color of that indicator to remain adhered to the outward-facing surface of the band. In order to effectuate this, a tamper-evident section of each indicator having the partial top surface of that indicator may be patterned and jointly configured with the adhesives such that a first adhesion strength between a first portion of the tamper-evident section and a second portion of the tamper-evident section is weaker than a second adhesion strength between the tamper-evident section and the outward-facing surface of the band. Put differently, upon attempted removal of the indicator(s), a residual visual portion may be left on the band that inhibits simple removal of an indicator without damaging the indicator and/or the band to which the indicator had been applied.

In some forms, each length of flexible indicator material may include an antimicrobial surface.

In some forms, the partial top surface of each indicator (or a greater portion of the indicator) may be supplied with an overprint varnish disposed above the indicium in which the overprint varnish protects the indicium against liquid exposure.

In some forms, the entire top surface of each indicator may be supplied with the overprint varnish.

In some forms, the underside of each indicator may include a bare area devoid of adhesive disposed between the first and second ends of that indicator. The bare area may have a length greater than the width of the strap at each respective location. The bare area of each indicator may include at least a first pair of alignment marks dimensioned to correspond to a width of the strap at a first respective location. The bare area of each indicator may also include at least a second pair of alignment marks dimensioned to correspond to a width of the strap at a second respective location and the width of the strap at the first respective location may be greater than the width of the strap at the second respective location. These marks can help to center the indicator on the band—even if the band has more than one width—and the lack of adhesive on the underside may help the individual applying the indicator to position the indicator relative to the band before adhesively securing it on the outwardly-facing side of the band.

In some forms, the strap may be formed from a first length of flexible strap material having a first end and a second end and may further include a closure mechanism that includes at least respective portions of the first and second ends of the strap. The closure mechanism may be configured to fasten the first and second ends of the strap together thereby forming the band into a closed loop dimensioned to encircle a limb of a patient.

According to another aspect, an indicator system is provided that includes a set of one or more flexible tamper-evident indicators for adhering to a band having a strap that forms a closed loop. Each of the set of one or more flexible tamper-evident indicators includes a respective length of flexible indicator material providing a top surface bearing an indicium on at least one of first and second ends of the indicator and further providing an underside. On the underside, adhesives are disposed at the first and second ends of the indicator and a bare area devoid of adhesive is disposed between the adhesives of the first and second ends of that indicator. The bare area has a length at least equal to a strap width of a selected band design.

In some forms, each indicator may be supplied with one or more removable liner films adhering to (or covering) the adhesives. The liner films may be configured to detach from the adhesives when the liner films are removed from the indicator. The indicators may be configured such that the liner films extend beyond one or more edges of each respective length of flexible indicator material. The liner films may be further configured to detach from the adhesives when pulled in a direction substantially parallel to the respective lengths of flexible indicator material. Among other things, this can accommodate easy attachment of the indicators, even if the individual attaching the indicators is wearing gloves or has limited use of both hands at the time of application.

In some forms, the bare area of each indicator may include at least a first pair of alignment marks dimensioned to correspond to the strap width of the selected band design and each indicator may be configured such that, when an indicator axis intersecting the first and second ends of the indicator is oriented perpendicularly to a strap of a band having the selected band design and the strap of that band is positioned to contact the bare area of the indicator between the first pair of alignment marks, the strap of that band contacts only the bare area of the indicator.

In some forms, the indicium of each indicator may be included in (or overlay) a tamper-evident section of the top surface of each indicator. The tamper-evident section of each top surface may be patterned and jointly configured with the adhesives such that a first adhesion strength between a first portion of the tamper-evident section and a second portion of the tamper-evident section is weaker than a second adhesion strength between the tamper-evident section and the outward-facing surface of the band. In such arrangement, when any indicator has been adhered to a band, subsequent removal of that indicator may cause at least a portion of the indicium of that indicator to remain adhered to the band.

In some forms, the adhesives may be jointly configured and dimensioned such that removal of any indicator causes at least a portion of the partial top surface of that indicator having a color of that indicator to remain adhered to the outward-facing surface of the band.

According to still yet another aspect, a method of adhering a tamper-evident indicator to a band having a strap that forms a closed loop is provided in which the tamper-evident indicator has a structure of a kind discussed above and elsewhere herein. The method includes positioning the indicator such that an indicator axis intersecting the first and second ends of the indicator is oriented perpendicularly to the strap and the bare area faces toward an inward-facing surface of the strap (which inward-facing surface faces toward a center of the closed loop, when formed). Then, the indicator is folded such that the adhesives adhere the first and second ends of the indicator to an outward-facing surface of the strap and such that the indicium faces outward from the center of the loop.

In some forms, the method may further include the steps of assembling the band to form the closed loop encircling a limb of a patient, inserting the indicator between the strap and the limb of the patient (such that the top surface of the indicator faces the limb and the underside of the indicator faces the strap), and exposing the adhesives by detaching liner materials adhered to the indicator by the adhesives.

These and still other advantages of the invention will be apparent from the detailed description and drawings. What follows is merely a description of some preferred embodiments of the present invention. To assess the full scope of the invention the claims should be looked to as these preferred embodiments are not intended to be the only embodiments within the scope of the claims.

BRIEF DESCRIPTION OF THE FIGURES

Advantages of embodiments of the present invention will be apparent from the following detailed description of the exemplary embodiments thereof, which description should be considered in conjunction with the accompanying drawings in which.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description, discussion of several terms used herein follows.

The word "exemplary" is used herein to mean "serving as an example, instance, or illustration." Any embodiment described herein as "exemplary" is not necessarily to be construed as preferred or advantageous over other embodiments. Likewise, the terms "embodiments of the invention," "embodiments," or "invention" do not require that all embodiments of the method, system or apparatus include the discussed feature, advantage or mode of operation.

Terms indicating relative position such as "above," "below," "upper," "lower," "rear," "front," and so forth are used for purposes of illustration only, unless otherwise noted and are made with reference to the orientation of the drawings. It should be understood that these terms are not generally meant to indicate a preferred orientation when such an orientation is not inherently or explicitly required.

Reference will be made throughout to applications of embodiments disclosed herein to medical settings, including identification bands worn by patients and indicators adhered to such bands. Such references are for purposes of illustration and are not intended to limit the claimed invention to such applications.

Figure 1A:
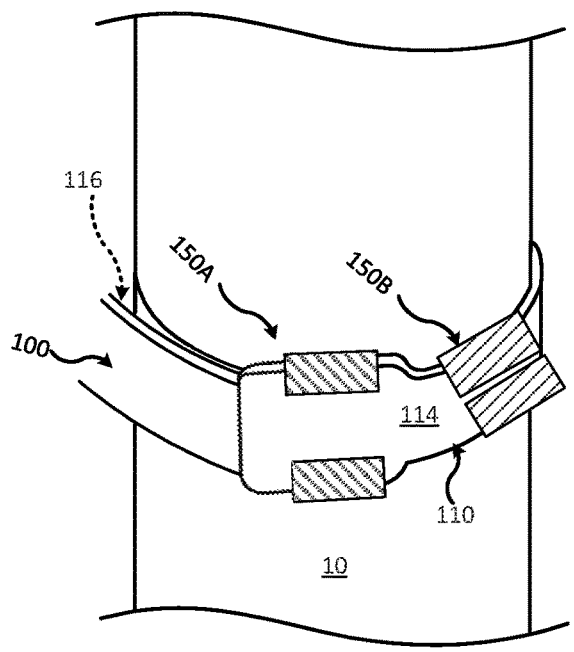
FIG. 1A schematically depicts an example embodiment including a strap having tamper-evident indicators in which the strap surrounds a wrist or ankle in closed loop form.

Looking first at FIG. 1A, an example embodiment comprising a band 100 is shown schematically surrounding a wrist-like or ankle-like structure (hereinafter referred to as wrist 10). The band 100 comprises a strap 110. The strap 110 has an outward-facing surface 114 and inward-facing surface 116 (not visible in FIG. 1A and indicated by a dashed arrow, but better seen in FIG. 1C) opposite the outward-facing surface 114. Also shown for illustration in FIG. 1B, in which the band 100 is shown in an un-looped or flat form, is a strap axis 140 indicated by a dashed arrow. References made to length(s) of the strap 110 refer to directions parallel to the strap axis 140, while references made to width(s) of the strap 110 refer to a direction perpendicular to the strap axis 140 and in the plane of the strap 110 when the strap 110 lies flat as shown in FIGS. 1B and 1C.

A set of indicators 150, which are tamper-evident, is represented by two indicators 150A and 150B shown affixed to the strap 110 at two different locations in which each of the two locations on the strap 110 have a different width. Although not necessarily shown to scale, the indicators 150A and 150B are each formed from a single respective length of flexible material. Indicators 150A and 150B are affixed by their ends to the outward-facing surface 114 of the strap 110 and wrap around the inward-facing surface 116 of the strap 110, as further described below in connection to FIGS. 1B and 1C.

Figure 1B:
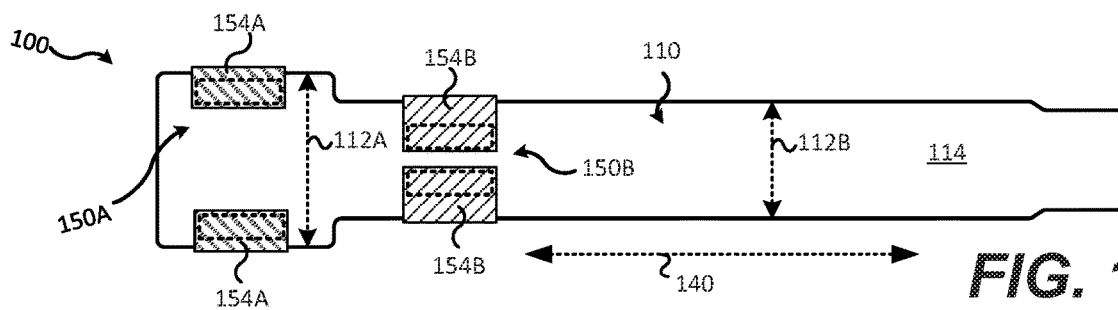
FIGS. 1B and 1C respectively depict top and bottom views of the example embodiment of FIG. 1A in which the band is in a non-looped or a flattened form.
Figure 1C:
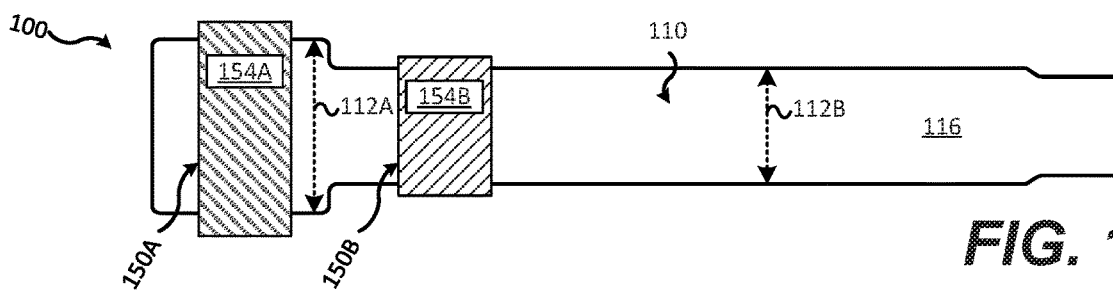

FIGS. 1B and 1C illustrate elements of the indicators 150A and 150B and their relation to elements of the strap 110 in greater detail. FIG. 1B shows a view of the outward-facing surface 114 of the strap 110 with indicators 150 affixed. In some embodiments, such as the band 100, the strap 110 has areas with different widths. Indicator 150A is shown affixed to the strap 110 at a first location having a width 112A, while indicator 150B shown affixed to the strap 110 in a second location having a narrower width 112B. It will be appreciated that while the band illustrated has a "flag" section that is wider than the remainder of the strap, that other bands could have a wider section intermediate to two strap sections of reduced width.

Figure 2:
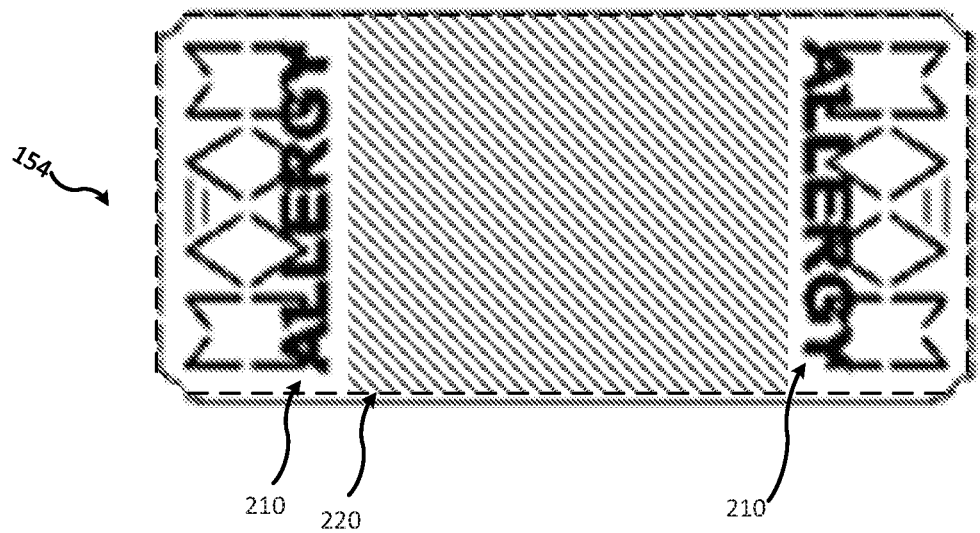
FIGS. 2 and 3 respectively depict top and bottom surfaces of an example tamper-evident indicator corresponding to the indicators depicted in FIGS. 1A, 1B, and 1C and showing further structural details of the indicator.

Each indicator 150, as disclosed herein, has a top surface 154, represented sections in FIGS. 1B and 1C by the top surface 154A of indicator 150A and the top surface 154B of indicator 150B (see also FIG. 2). Each indicator 150 also has an underside 156 shown and described below in connection to FIG. 3).

As noted above, each indicator 150 is affixed to the outward-facing surface 114 of the strap. Each indicator 150 is affixed using adhesives beneath the top surface 154 of that indicator 150, as indicated by the dashed regions shown with the top surface 154A in FIG. 1B.

Figure 3:
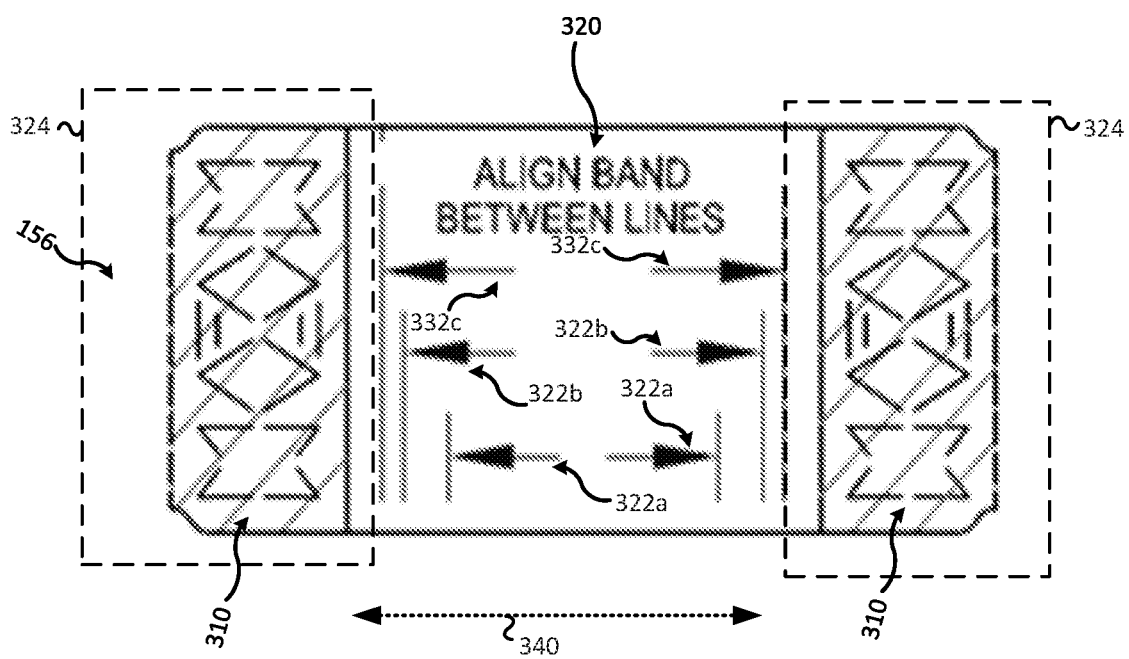

FIG. 2 and FIG. 3 respectively show the top surface 154 and underside 156 of an example indicator 150 without the indicator 150 being wrapped around a band to better show its unattached structure.

As shown in FIG. 2, each indicator 150 has tamper-evident sections ("TE sections 210") belonging to the top surface 154, preferably one at each end of the indicator 150. In some embodiments, each TE section 210 forms or otherwise includes an indicium. As shown in FIG. 2, such an indicium may include text such as the text "ALLERGY", shown as a non-limiting example. Such an indicium or similar indicia may be useful in medical applications where it is important to identify patients with medication allergies, or other conditions. In such applications, the indicator 150 is adhered to the band 100 (which may be a medical identification band) as shown in FIGS. 1A, 1B, and 1C and the indicium can be visible, even when the band 100 is formed into a loop. In some embodiments, the indicator 150 includes a particular color forming part of the indicium or as an additional indicium, as indicated by hatching in the area 220 of FIG. 2 (note the TE sections 210 are shown without hatching so the TE sections 210 and their indicia may be seen clearly, but any coloration could also be found in the TE sections 210 as well). In the case of a pre-defined set of indictors, different colors can be associated with different conditions (e.g., red as allergy, yellow as fall risk, purple as do not resuscitate, pink as limb alert, and green as no latex, for example). In this way, an observer familiar with the indicator set may be able to determine quickly the condition flagged by the indicator from afar, even if the indicium is not readable at the distance.

In some embodiments, the indicator 150 (or appropriate parts thereof such as areas with text) is provided with an overprint varnish (OPV) to protect indicia and/or other parts from liquid exposure. In some embodiments, no part of the indicator 150 is supplied with such an OPV. In addition, the indicator 150 may include one or more antimicrobial surfaces for use in medical and other settings to reduce the spread of infectious diseases and organisms.

Below, tamper-evident features of the TE sections 210 and other features of the indicator 150 are described in connection with FIG. 3.

FIG. 3 shows the underside 156 of the indicator 150. The undersides 310 of the TE sections 210 are areas supplied with the adhesives (indicated by light hatching). Also visible are example tamper-evident features. As shown, the TE sections 210 (as visible in FIG. 2 and in FIG. 3 at the undersides 310) are patterned with various features. These patterns—which may be, for example, scored or die cut—define regions designed to tear away from the rest of the TE section 210 if the indicator 150 is removed from a surface after it has been adhered to that surface. In practice this may be accomplished by making the adhesion force between the patterned areas and the rest of the TE sections 210 weaker than the adhesion between the rest of the TE sections 210 and the surface (such as the outward-facing surface 114 of the strap 110). In this example, portions of the text will remain on the surface if the indicator 150 is removed, allowing remnants of the TE section 210 which remain adhered to the surface continue to function as the indicia, or at the very least to signal that one or more indicia were formerly present. It should be understood that the foregoing description of the TE sections 210 is intended as non-limiting example and that any tamper-evident design enabling the functionalities described herein is suitable.

Also visible on the underside 156 in FIG. 3 is a bare area 320 devoid of adhesive. In certain embodiments, the bare area 320 includes pairs of alignment marks 322, represented in FIG. 3 by the three pairs of alignment marks 322a, 322b, and 322c.

In certain embodiments, the indicator 150 is also supplied with removable liner materials 324 which protect the adhesives on the undersides 310 of the TE sections 210. The liner materials 324 may be thin strips of plastic or other material that are configured to readily separate from the indicator 150 when pulled.

Now that structural features of the band 100 and indictors 150 have been described, methods of using the band 100 with indicators 150 will be described with reference to these figures. For purposes of illustration and discussion, it is here noted that FIG. 3 shows a dashed arrow representing an indicator axis 340. References to length(s) of the indicator 150 refer to directions parallel to the indicator axis 340 and references to width(s) of the indicator 150 refer to directions perpendicular to the indicator axis 340 in the plane of the indicator 150 when the indicator 150 lies flat as shown in FIG. 3.

In an example method of applying an indicator 150 to a band such as the band 100, a user positions the indicator 150 within the closed loop formed by band 100 such that the underside 156 of the indicator 150 faces the inward-facing surface 116 (which is opposite the outward-facing surface 114) of the strap 110. The user optionally aligns the strap 110 such that it is centered within an appropriate pair of alignment marks 322 on the bare area 320 on the underside 156 of the indicator 150. With the indicator 150 so positioned, the user removes the liner materials 324 and folds the indicator 150 around the strap 110 such that the undersides 310 of the TE sections 210 (and the adhesives disposed thereon) contact the outward-facing surface 114 of the strap 110, thereby adhering the indicator 150 to the strap 110. It is contemplated this could be done in a stepwise fashion, with one of the liners 324 being removed and the corresponding underside 310 folded over before the other liner 324 and underside 310 are handled, or both liners 324 could be removed before attachment of either of the undersides 310.

When embodiments disclosed herein are used as described, various features of said embodiments may provide particular advantages. For one, the TE sections 210 of the indicators 150 can address common shortcomings of conventional approaches such as the tendency for indicators to fall off or be removed in such a way that detachment of the indicator cannot be easily detected. When an indicator 150 employs TE sections 210 detachment of the indicator 150 from the band 100, the indicating objective of the indicator 150 is thus still accomplished by the remnant(s) of the indicator. Alternatively, even if remnant(s) of the indicator no longer function for that purpose, the remnant(s) still serve as an indication that an indicator 150 was previously present and that the band 100 (and/or a wearer of the band 100, such as a patient) should receive appropriate attention (for example, a doctor or nurse may realize that it is necessary to check the patient's records and apply replacement indicators 150 as needed).

The placement of the adhesives on the undersides 310 of the TE sections 210, together with the liner materials 324, can also address additional shortcomings of conventional indicators. For example, conventional stickers (with adhesive covering an entire side of the sticker) wrapped around a patient identification band will tend to adhere to a patient's skin or body hair, making application of the sticker difficult for the user and uncomfortable for the patient. In addition, once a sticker's adhesive is exposed in preparation for use, parts of the sticker's may stick to the user's finger or parts of the sticker may stick to themselves. These issues may be exacerbated in settings where the stickers are applied by users who must wear gloves to avoid contamination and infection. Indicators 150 disclosed herein address these issues by providing the bare area 320 that is devoid of adhesive and the liner materials 324 which covers the adhesives prior to use.

When the liner materials 324 are provided as shown in FIG. 3, they allow a user to position the indicator 150 with no risk of accidental adhesion of the indicator 150 to surfaces other than the desired surface of the band 100. The liner materials 324 may dimensioned in the oversized fashion shown in FIG. 3 to allow easy removal of the liner materials 324 by users with reduced dexterity (such as nurses and doctors wearing gloves).

In an example application procedure, a user positions the indicator 150 beneath the band 100 as previously described above. The user can holds the indicator 150 in place by pinching the indicator 150 and the strap 110 together between the user's thumb and forefinger with the user's forefinger (for example) resting on the inward-facing surface 116 of the strap 110. The user then removes the liner materials 324 with the other hand. The user may now user flip one of the TE sections 210 upward and roll it over onto the outward-facing surface 114 of the strap 110, pressing until it adheres to the strap 110. This maneuver may then be repeated with the other TE section 210. It will be appreciated that while there is a small gap between the ends in the illustrated figures on the outward facing surface 114, that in some forms, the ends of the adhered sections could meet or at least in part overlap each other; however, even in such overlapping form, one of the ends will adhesively attach to the underlying band.

It will be observed from this description of application that such indicators should have a length in excess of the width of the band to which the indicator is to be applied so that the partial top surfaces of the indicator on the outside of the band are visible after application. However, in a general sense, the overall length of the indicator will not likely be more than three times the width of the band to which the indicator is to be applied as that would leave excess material, even if the two ends are fold completely onto one another on the outwardly facing surface. Even so, this leaves a significant amount of possible length variance that is acceptable and a single length of indicator could be used on range of various width bands.

Thus, systems and methods including tamper-evident indicators applied to a band comprising a strap and forming a closed loop have been disclosed. Tamper-evident sections of the indicators provide increased security against accidental and intentional removal of the indicators. Indicators are provided with adhesives and bare areas devoid of adhesive allowing easy and secure application of indicators to bands worn by humans and animals with greater ease. Indicators are further provided with liners protecting the adhesives allowed indicators to be easily applied by gloved hands, reducing contamination risks. Contamination and wear risks are further reduced by supplying indicators with antimicrobial surfaces and overprint varnishing.

It will further be appreciated that such indicators may be provided in many forms. For example, the indicators may be provided on rolls containing a length from which an individual indicator is separable by virtue of scoring, perforations or so forth or which may be die cut on a continuous supportive release liner such that individual indicators may be removed. Still further the roll might be received on a dispenser that is able to hold one or more rolls, with each of the rolls having a unique type of indicator contained thereon (i.e., one roll for "fall risk" indicators, one roll for "allergy" indicators, one roll for "no latex" indicators and so forth). In some forms, these rolls not have indicium pre-printed on them and they may be fed into a printer so that the indicium may be printed on them prior to application. Still yet, such lengths may come in folded over in accordion fashion. Still further, the indicators could be sold as part of an alert kit which includes a roll of each type of alert per box or just one type of alert in multiple sizes. Furthermore, when on a roll, there can be a "notch" between adjacent ends of indicators for improved ease of separation.

Still further, while such bands and indicators have been described primarily in a medical setting, it will be appreciated that such banding and indicator systems could be employed in other contexts outside of the healthcare market as well. For example, such contexts could include hotels/resorts, festivals, concerts, and other entertainment venues to visually indicate access to certain sections or areas using a single band with multiple identifiers.

Although specific embodiments are described above, it will be apparent to those of ordinary skill that a number of variations can be made within the scope of the disclosure. It should be understood, therefore, that the methods and apparatuses described above are only exemplary and do not limit the scope of the invention, and that various modifications could be made by those skilled in the art. To apprise the public of the scope of this invention, the following claims are made.

What is claimed is:

1. An assembly comprising:
  a band including a strap that forms a closed loop; and
  a set of one or more flexible tamper-evident indicators formed from respective lengths of flexible indicator material, each indicator having first and second ends, each indicator being adhesively fastened by adhesives disposed at the first and second ends of that indicator to the band at a respective location on the strap, the respective location on the strap having a width smaller than each of the respective lengths of flexible indicator material;
  wherein the adhesives are disposed on an underside of each indicator and each indicator is configured such that a partial top surface of that indicator overlays an outwardly-facing surface of the strap at the first and second ends of that indicator, the partial top surface bearing an indicium;
  wherein the outwardly-facing surface of the strap and the partial top surface of each indicator face away from a center of the closed loop;
  wherein the set of one or more flexible tamper-evident indicators includes at least first and second indicators;
  wherein the first indicator has a first color and bears a first indicium on its partial top surface; and
  wherein the second indicator has a second color and bears a second indicium on its partial top surface.

2. The assembly of claim 1,
  wherein the strap is formed from a first length of flexible strap material having a first end and a second end; and
  wherein the band further comprises a closure mechanism that includes at least respective portions of the first and second ends of the strap, the closure mechanism configured to fasten the first and second ends of the strap together, forming the band into a closed loop dimensioned to encircle a limb of a patient.

3. An assembly, comprising:
  a band including a strap that forms a closed loop; and
  a set of one or more flexible tamper-evident indicators formed from respective lengths of flexible indicator material, each indicator having first and second ends, each indicator being adhesively fastened by adhesives disposed at the first and second ends of that indicator to the band at a respective location on the strap, the respective location on the strap having a width smaller than each of the respective lengths of flexible indicator material;
  wherein the adhesives are disposed on an underside of each indicator and each indicator is configured such that a partial top surface of that indicator overlays an outwardly-facing surface of the strap at the first and second ends of that indicator, the partial top surface bearing an indicium;
  wherein the outwardly-facing surface of the strap and the partial top surface of each indicator face away from a center of the closed loop;
  wherein the indicators and the adhesives are jointly configured and dimensioned such that removal of any indicator causes at least a portion of the partial top surface of that indicator having a color of that indicator to remain adhered to the outward-facing surface of the band; and
  wherein a tamper-evident section of each indicator having the partial top surface of that indicator is patterned and jointly configured with the adhesives such that a first adhesion strength between a first portion of the tamper-evident section and a second portion of the tamper-evident section is weaker than a second adhesion strength between the tamper-evident section and the outward-facing surface of the band.

4. An assembly, comprising:
  a band including a strap that forms a closed loop; and
  a set of one or more flexible tamper-evident indicators formed from respective lengths of flexible indicator material, each indicator having first and second ends, each indicator being adhesively fastened by adhesives disposed at the first and second ends of that indicator to the band at a respective location on the strap, the respective location on the strap having a width smaller than each of the respective lengths of flexible indicator material;
  wherein the adhesives are disposed on an underside of each indicator and each indicator is configured such that a partial top surface of that indicator overlays an outwardly-facing surface of the strap at the first and second ends of that indicator, the partial top surface bearing an indicium;
  wherein the outwardly-facing surface of the strap and the partial top surface of each indicator face away from a center of the closed loop; and
  wherein each length of flexible indicator material includes an antimicrobial surface.

5. An assembly, comprising:
  a band including a strap that forms a closed loop; and
  a set of one or more flexible tamper-evident indicators formed from respective lengths of flexible indicator material, each indicator having first and second ends, each indicator being adhesively fastened by adhesives disposed at the first and second ends of that indicator to the band at a respective location on the strap, the respective location on the strap having a width smaller than each of the respective lengths of flexible indicator material;
  wherein the adhesives are disposed on an underside of each indicator and each indicator is configured such that a partial top surface of that indicator overlays an outwardly-facing surface of the strap at the first and second ends of that indicator, the partial top surface bearing an indicium;
  wherein the outwardly-facing surface of the strap and the partial top surface of each indicator face away from a center of the closed loop; and
  wherein at least the partial top surface of each indicator is supplied with an overprint varnish disposed above the indicium, the overprint varnish protecting the indicium against liquid exposure.

6. The assembly of claim 5, wherein the entire top surface of each indicator is supplied with the overprint varnish.

7. An assembly, comprising:
a band including a strap that forms a closed loop; and
a set of one or more flexible tamper-evident indicators formed from respective lengths of flexible indicator material, each indicator having first and second ends, each indicator being adhesively fastened by adhesives disposed at the first and second ends of that indicator to the band at a respective location on the strap, the respective location on the strap having a width smaller than each of the respective lengths of flexible indicator material;
wherein the adhesives are disposed on an underside of each indicator and each indicator is configured such that a partial top surface of that indicator overlays an outwardly-facing surface of the strap at the first and second ends of that indicator, the partial top surface bearing an indicium;
wherein the outwardly-facing surface of the strap and the partial top surface of each indicator face away from a center of the closed loop; and
wherein the underside of each indicator includes a bare area devoid of adhesive disposed between the first and second ends of that indicator, the bare area having a length greater than the width of the strap at each respective location.

8. The assembly of claim 7, wherein the bare area of each indicator includes at least a first pair of alignment marks dimensioned to correspond to a width of the strap at a first respective location.

9. The assembly of claim 8,
wherein the bare area of each indicator includes at least a second pair of alignment marks dimensioned to correspond to a width of the strap at a second respective location; and
wherein the width of the strap at the first respective location is greater than the width of the strap at the second respective location.

10. An indicator system comprising a set of one or more flexible tamper-evident indicators for adhering to a band having a strap that forms a closed loop, each of the set of one or more flexible tamper-evident indicators comprising a respective length of flexible indicator material providing a top surface bearing an indicium on at least one of first and second ends of the indicator and an underside with adhesives disposed thereon at the first and second ends of the indicator and with a bare area devoid of adhesive disposed between the adhesives of the first and second ends of that indicator, the bare area having a length at least equal to a strap width of a selected band design;
wherein each indicator is supplied with one or more removable liner films adhering to the adhesives, the liner films configured to detach from the adhesives when the liner films are removed from the indicator;
wherein the bare area of each indicator includes at least a first pair of alignment marks dimensioned to correspond to the strap width of the selected band design; and
wherein each indicator is configured such that, when an indicator axis intersecting the first and second ends of the indicator is oriented perpendicularly to a strap of a band having the selected band design and when the strap of that band is positioned to contact the bare area of the indicator between the first pair of alignment marks, the strap of that band contacts only the bare area of the indicator.

11. The system of claim 10, wherein the indicators are configured such that the liner films extend beyond one or more edges of each respective length of flexible indicator material.

12. The system of claim 11, wherein the liner films are further configured to detach from the adhesives when pulled in a direction substantially parallel to the respective lengths of flexible indicator material.

13. An indicator system comprising a set of one or more flexible tamper-evident indicators for adhering to a band having a strap that forms a closed loop, each of the set of one or more flexible tamper-evident indicators comprising a respective length of flexible indicator material providing a top surface bearing an indicium on at least one of first and second ends of the indicator and an underside with adhesives disposed thereon at the first and second ends of the indicator and with a bare area devoid of adhesive disposed between the adhesives of the first and second ends of that indicator, the bare area having a length at least equal to a strap width of a selected band design;
wherein the indicium of each indicator is included in a tamper-evident section of the top surface of each indicator;
wherein the tamper-evident section of each top surface is patterned and jointly configured with the adhesives such that a first adhesion strength between a first portion of the tamper-evident section and a second portion of the tamper-evident section is weaker than a second adhesion strength between the tamper-evident section and the outward-facing surface of the band; and
wherein, when any indicator has been adhered to a band, subsequent removal of that indicator causes at least a portion of the indicium of that indicator to remain adhered to the band.

14. An indicator system comprising a set of one or more flexible tamper-evident indicators for adhering to a band having a strap that forms a closed loop, each of the set of one or more flexible tamper-evident indicators comprising a respective length of flexible indicator material providing a top surface bearing an indicium on at least one of first and second ends of the indicator and an underside with adhesives disposed thereon at the first and second ends of the indicator and with a bare area devoid of adhesive disposed between the adhesives of the first and second ends of that indicator, the bare area having a length at least equal to a strap width of a selected band design;
wherein the adhesives are jointly configured and dimensioned such that removal of any indicator causes at least a portion of the partial top surface of that indicator having a color of that indicator to remain adhered to the outward-facing surface of the band.

15. A method of adhering a tamper-evident indicator to a band having a strap that forms a closed loop, the tamper-evident indicator having a length of flexible indicator material providing a top surface bearing an indicium on a tamper-evident section of the top surface at one or more of first and second ends of the indicator and further having an underside with adhesives disposed thereon at the first and second ends of the indicator and with a bare area devoid of adhesive disposed between the adhesives of the first and second ends of that indicator, the bare area having a length at least equal to a width of the strap, the method comprising:
positioning the indicator such that an indicator axis intersecting the first and second ends of the indicator is oriented perpendicularly to the strap and the bare area faces toward an inward-facing surface of the strap which faces toward a center of the closed loop; and folding the indicator such that the adhesives adhere the first and second ends of the indicator to an outward-facing surface of the strap and such that the indicium faces outward from the center of the loop.

16. The method of claim 15 further comprising:

assembling the band to form the closed loop encircling a limb of a patient;

inserting the indicator between the strap and the limb of the patient such that the top surface of the indicator faces the limb and the underside of the indicator faces the strap; and exposing the adhesives by detaching liner materials adhered to the indicator by the adhesives.

\* \* \* \* \*